United States Patent [19]

Harich et al.

[11] 4,021,577

[45] May 3, 1977

[54] USEFUL PRODUCT DERIVED FROM GRAPEFRUIT PULP AND PROCESS FOR PREPARING THE SAME

[75] Inventors: Jakob Harich; Franz P. Harich, both of Orlando, Fla.

[73] Assignee: Rush-Hampton, Inc., Orlando, Fla.

[22] Filed: May 2, 1975

[21] Appl. No.: 573,900

Related U.S. Application Data

[60] Division of Ser. No. 126,251, March 19, 1971, Pat. No. 3,890,212, which is a continuation-in-part of Ser. No. 27,080, April 9, 1970, abandoned.

[52] U.S. Cl. ............................ 424/195; 204/158 R
[51] Int. Cl.$^2$ ..................... A61K 35/78; G01J 1/10
[58] Field of Search ................. 424/195; 204/158 R

[56] References Cited

OTHER PUBLICATIONS

Dadak et al.–Chem. Abst., vol. 64, (1966), p. 8780h.
U.S. Dispensatory–25th Edition, (1955), pp. 612, 1038, 1039 and 1135.

*Primary Examiner*—Sam Rosen
*Attorney, Agent, or Firm*—Jerry D. Voight

[57] ABSTRACT

Grapefruit pulp is reacted with an alcohol or ketone, preferably a polyhydric alcohol such as propylene glycol or glycerin, in the presence of a free radical initiator such as ultraviolet light to produce a stable reaction product useful as an ingredient in various cosmetic products and for other purposes. The product is also highly effective as an antibacterial and antifungal agent.

13 Claims, 2 Drawing Figures

USEFUL PRODUCT DERIVED FROM GRAPEFRUIT PULP AND PROCESS FOR PREPARING THE SAME

This application is a divisional of application Ser. No. 126,251, filed Mar. 19, 1971, now U.S. Pat. No. 3,890,212, which application is a continuation-in-part of U.S. application Ser. No. 27,080, filed Apr. 9, 1970, now abandoned.

This invention relates to the preparation and use of new compounds from citrus products. More particularly, it relates to novel compounds prepared from grapefruit pulp, to the processes for preparing these compounds, and to compositions and methods for their effective use.

The citrus industry is an important segment of the economy of Florida, California, and other parts of the United States. This industry has heretofore largely centered on the production of citrus food products such as orange juice, grapefruit juice and the like.

Large quantities of certain portions of citrus products such as rind, pulp and the like are presently considered to be waste and are merely destroyed or thrown away by commercial fruit or juice processing operations. For a number of years, however, citrus products have been viewed as a vast, largely untapped reservoir of new chemical materials which could be useful in fields widely divergent from the food industry.

At the same time, citrus products, because of their association with the outdoors, favorable weather conditions, and what may be generally termed a "fresh-air environment," have been extensively used in imparting fragrances to many types of products such as lemon sprays, deodorants and polishes, lemon and lime shave creams, and many other similar products. Deodorant products of this type have heretofore merely masked the air with a pleasant citrus-type odor, without eliminating the basic cause of the odor.

It is a primary object of the present invention to provide new compositions and products of citrus origin, and more particularly from the pulp of grapefruit.

It is a further object of one embodiment of this invention to provide a novel air purifier and sanitizing composition derived from grapefruit pulp.

An object of another embodiment of the invention is to provide a new skin conditioning and cosmetic additive composition.

Still another object of this invention is to provide processes for the production of the new compositions and products of this invention.

Additional objects and advantages of the invention will be set forth in part in the description that follows and in part will be obvious from that description or may be learned by practice of the invention, the objects being realized and attained by means of the compositions, methods, processes, steps and procedures particularly pointed out in the appended claims.

In accordance with this invention, a process is provided for preparing a novel, citrus-based composition which is an excellent air purifier, deodorizer, and antibacterial and antifungal agent. This process comprises reacting grapefruit pulp with an alcohol or ketone, preferably a polyhydric alcohol such as propylene glycol or glycerin, to produce a stable reaction product which is useful in many applications, particularly in skin treatment and conditioning and as an ingredient of various types of cosmetic preparations.

The invention consists of the novel steps, methods, processes, procedures, compositions, products and improvements shown and described.

The accompanying drawings, which are incorporated in and constitute a part of this specification, illustrate one embodiment of an apparatus which can be used to practice the process of this invention and, together with the description, serve to explain the principles of the invention.

Figure 1:
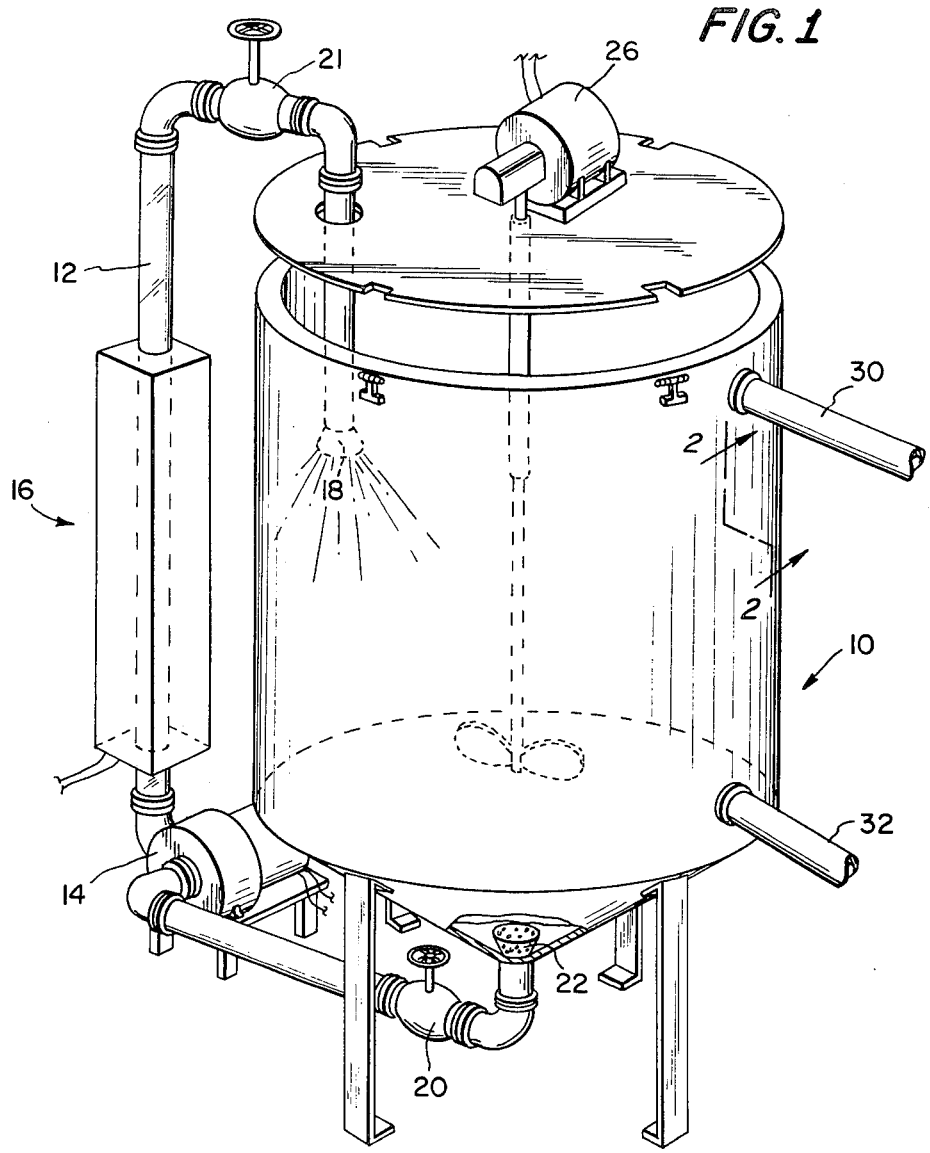
FIG. 1 shows a perspective view of an apparatus useful in practicing the process of this invention.

In accordance with the invention, the starting material of the present process comprises grapefruit pulp. This pulp is located immediately under the hard, outer rind layer of the skin of fresh grapefruit and is obtained by mechanically shaving the rind portion from the skin, normally after the inner juice, meat and section skins have been previously removed. The separation of the rind from the inner pulp layer of the skin should be accomplished in such a manner that the inner pulps are not damaged.

The pulps used are preferably acquired from fresh, ripe grapefruit obtained when the acid content of the fruit is low, as shown by a pulp pH of about 2.5 to 5.0, and preferably 3.5 to 5.0. The pulp is preferably obtained during the December through April grapefruit season in Florida, and used while it is fresh, for example, after storage at 40° to 45° F for a period of not over about 3 days. Longer storage times, up to several months or longer, can be achieved by adding the alcohol or ketone reactant, e.g., propylene glycol or glycerin, to the pulp and storing the two together.

In accordance with the present invention, the grapefruit pulp is reacted with the alcohol or ketone, preferably at an elevated temperature and under the influence of ultraviolet radiation, to produce a stable reaction product.

Both monohydric and polyhydric alcohols can be used in this first stage reaction. Thus, suitable alcohols include methanol, ethanol, isopropanol, n-propanol, n-butanol, allyl alcohol, amyl alcohol, tert-amyl alcohol, octyl alcohol, benzyl alcohol, ethylene glycol, propylene glycol, diethylene glycol, dipropylene glycol, triethylene glycol, tetraethylene glycol, glycerin and the like. Acetone is the presently preferred ketone reactant.

The polyhydric, aliphatic alcohols such as propylene glycol and glycerin are greatly preferred reactants in the present process, and, in fact, appear to yield significantly and even unexpectedly superior results over the other alcohol or ketone reactants which can also be used.

The reaction is carried out at room temperature or above, with the reaction proceeding more rapidly at somewhat elevated temperatures. Reaction temperatures of 90° to 140° F are generally used, and temperatures of 110° to 120° F are preferred.

The ratio of alcohol or ketone to grapefruit pulp used in the reaction can be varied widely. Most of the alcohol used in the preferred procedure described below does not enter into a reaction with the pulp and is believed to serve only a mechanical or extractive function, if any. It is to be understood that the term "reaction" as used here is intended to have its broadest meaning and includes extractive reactions or any other chemical mechanism tht may occur as a result of the practice of the first step of the present process. An excess of alcohol (i.e., propylene glycol) reactant is presently preferred and the reaction is generally carried out using a weight ratio of grapefruit pulp to propylene glycol or glycerin of about 1:2. This ratio of reactants has been generally found to yield a superior quality and quantity of intermediate reaction product. Depending on many factors such as frosts, application of pesticide to the fruit, etc., it may be desirable in some cases to vary the ratio of pulp to alcohol as low as 1:4.5 or even lower.

The reaction of the present invention is preferably carried out in the presence of a free radical initiator, most preferably ultraviolet (UV) light. Other conventional radical initiators, such as the chemical initiators tertiary butyl hydroperoxide, azobisbutyronitrile, dicumyl peroxide or the like can also be used. UV light has been found to function well in the present process and is presently preferred. The UV light may be supplied by commercially available UV light sources or even by sunlight.

A suitable system for carrying out this reaction is illustrated in the attached drawing. Referring to the drawing, 1 part by weight of grapefruit pulp is placed in a stainless steel reaction vessel indicated generally as 10, and 2 parts by weight of alcohol or ketone, preferably propylene glycol or glycerin, are added over the pulp and circulated through tank 10 and reaction tube 12 by means of pump 14. The reaction mixture in tank 10 is circulated through clear reaction tube 12, which is appropriately made of glass or clear plastic, such as polypropylene, Teflon, or Pyrex, for a period of about 6 to 24 hours preferably at a temperature of about 110° to 120° F. The mixture is subjected to ultraviolet radiation from UV source 16 during its passage through tube 12. This light can be supplied for example from a General Electric Black UV light source with integral Filter No. F 20T12-BL-20 watts, 24 inches long.

The mixture is, of course, continuously recirculated through the grapefruit pulp in reaction vessel 10. Referring again to the drawing, reaction vessel 10 can,for example, comprise stainless steel, steam-jacketed 252 gal. reaction vessel equipped with a 1.6 horsepower, 3400 rpm stainless steel pump 14. 1½ to 2-inch clear, plastic tubing 12 is provided for recirculation of the reaction mixture through a source of ultraviolet light 16. The light source can comprise 4 24 inch ultraviolet tubes of the type described above, with 2 tubes on each side of the plastic tubing and a 3½ inch center space between the sets of UV tubes.

The reaction mixture is preferably introduced back into tank 10 from tubing 12 through a sprinkle outlet 18. Two-way gate valves 20 and 21 allow the reaction mixture to be either recirculated by pump 14 or drained by gravity to remove it from the reaction vessel. This draining and recirculating preferably take place through a screen drain 22 located at the bottom of the reaction vessel. This drain can comprise, for example, a 16 mesh screen. Stirrer 24, driven by motor 26 can be used to achieve agitation if desired, although agitation is not required.

The propylene glycol, glycerin or other alcohol or ketone component used in the reaction is preferably U.S.P. grade. The reaction vessel is preferably operated at a pressure of about 5 to 20 p.s.i.g.

The reaction product produced in the first-stage reaction contains substantial amounts of unreacted propylene glycol or other alcohol or ketone and water, and a relatively minor amount of one or more active components which have not been totally identified. For example, at 1:2 ratios of pulp to propylene glycol, the reaction product is believed to contain about 80 to 90% unreacted propylene glycol, about 10% water and about 0.5 to 4% of active component or components. This reaction product is storage stable and is useful in the cosmetic and veterinary fields, particularly for application to the skin, for example, in treatment or conditioning of the epidermis, stratum corneun and sebaceous gland areas of human and animal tissue. It is believed that the active components of this product play an important role in conditioning cells, tissue, and fibrous membrane in the circulation system of the open skin surface.

This product has effective antibacterial and antifungal properties, particularly in purified form, and these may contribute to its beneficial effect in cosmetic preparations.

The reaction product of this invention thus is a highly beneficial, natural skin conditioner, which particularly improves the texture and softness of the horny layer and lipoidal portion of the skin of both humans and animals. The material may thus be incorporated in minor amounts of about 1 to 2% in conventional cosmetic bases such as cleansing cream, ointment or surfactants of the Tween-80 variety and applied as a cosmetic or softening agent to the skin.

This product can be beneficially incorporated in a wide variety of cosmetic products, for example, in suntan lotion, suntanning lotion, night cream, cleansing cream, moisture foundation cream, cream hair rinse, skin freshener, hand and body lotion, and anti-dandruff shampoos, among others. Suitable formulations for many of such products using the reaction product of the invention are illustrated in the specific examples set forth hereinafter, wherein the reaction product is referred to as "CA-90 Base." It is to be understood, however, that these particular formulations are only exemplary and that the compositions of this invention can be used in small amounts effective for skin conditioning, for example, on the order of about 0.5 to 2% by weight, in virtually any cosmetic base material for shampoos and other cosmetic formulations that contact the skin.

The following specific examples are presented to afford a better understanding of the present invention to those skilled in the art. It is to be understood that these examples are intended to be illustrative only and are not intended to limit the invention in any way.

EXAMPLE 1

Figure 2:
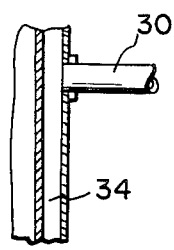
FIG. 2 shows in section the steam jacket used in heating the contents of the reaction vessel of FIG. 1.

One pound (454 gms.) of fresh grapefruit pulp prepared by mechanically removing the outer rind from the inner pulp of grapefruit picked 2 days previously is placed into a laboratory stainless steel reactor and 2 pounds (908 gms.) of propylene glycol U.S.P. is added over the grapefruit pulp. The liquid portion of the reaction mixture is circulated through the grapefruit pulp and through Teflon tubing surrounded by an ultraviolet light source, in a system of the type illustrated in the attached drawings, for a period of 24 hours. The system is maintained at a temperature of 110° to 120° F during this period. Heating is accomplished by introducing steam at 10–20 p.s.i.g. into steam jacket 34 (FIG. 2) through steam inlet 30. Outlet 32 allows removal of spent steam. The ultraviolet light source consists of four ultraviolet tubes, with two tubes located on each side of the clear, Teflon recycle tube.

A total of 872 gms. of liquid reaction product is then separated from the grapefruit pulp residue by straining through a 16 mesh screen. This reaction product is storage stable for an indefinite period of time.

EXAMPLE 2

The procedure of Example 1 is repeated in this example except that 2 parts by weight of glycerin are substituted for propylene glycol in the reaction step. The results achieved are substantially the same as those achieved in Example 1.

EXAMPLE 3

The process of Example 1 is repeated in this example, except that commercial size equipment is utilized. A stainless steel tank having a capacity of 252 gals., and a 1½ in. diameter polypropylene tubing is used to cycle the reaction mixture through the pulp and ultraviolet light source. That UV source comprises for 24 in. ultraviolet tubes, with two tubes set on each side of the tubing. The space between the opposing sets of tubes is 3½ in.

One hundred (100) lbs. of fresh grapefruit pulp which has been stored for 1 day at 40° to 45° F is added to the reactor and 200 lbs. of propylene glycol U.S.P. is added through a monitoring pump. The reaction is carried out at 110° to 120° F with constant cycling for a period of 12 hours and 195 lbs. of liquid reaction product is then separated by draining from the reaction vessel through a 16 mesh filtration screen. A portion of this reaction product is stored and again found to be storage stable for an indefinite period of time.

EXAMPLE 4

The procedure of Example 3 is repeated in this example except that during the initial reaction between the grapefruit pulp and the propylene glycol, a cloudy, unstable reaction product is produced. It is believed that this instability is probably due to hard frost encountered by the fruit during its growth. The reaction is stopped after about 6 hrs. and additional propylene glycol is added to reduce the ratio of pulp to propylene glycol to about 1:4.5.

EXAMPLE 5

In this example various alcohols, ketones and other solvents are substituted for the propylene glycol or glycerin reactant used in the reaction of Example 1-4 above. The procedure of Example 1 is generally followed, using 50 grams of grapefruit pulp and 100 grams of alcohol, ketone or other reactant. The reaction is carried out under UV light at temperatures ranging from 90° to 190° F, for reaction times between 12 and 24 hours.

The reaction products of these reactions are filtered, diluted 50/50 with methanol, heated slightly to 90°-110° F and then allowed to set for about 10 minutes. Eight (8) ml. samples are then centrifuged and the upper liquid phase decanted to leave a small accumulation of a brown gel-type material in the bottom of the tubes used in centrifuging. The total amount of this gel produced in each of the reactions is accumulated and weighed. The gel is washed with acetone and all liquid removed by vacuum. The amounts and nature of the products produced in reactions of grapefruit pulp with various alcohols, ketones and other typical solvent reactants are shown in Table II below When this gel product is placed under refrigeration at 25° to 30° F for about 72 hours, the formation of white crystals is observed. These crystals are washed with cold water and filtered. They are soluble in hot water and insoluble in either and chloroform. The brownish gel is preferably exposed to sunlight and open air for several days before this crystal recovery process is instituted. This results in the gel being modified to have a yellow syrup-like appearance. These crystals, prepared by reacting grapefruit pulp with acetone, isopropanol and propylene glycol and diluted 1 to 100 with hot water, are effective against bacteria as shown by the following tests. A combination of two cultures are used in the tests – *Staphylococcus aureus* gram negative and gram positive. These cultures are inoculated on the surface of test plates covered with freshly prepared Nutrient Agar media. Test filters previously dipped in the compositions of the invention and control filters dipped in propylene glycol are placed in the center of the plates and the plates are incubated for 48 hours at 37.5° C. The effectiveness of the compositions against the bacteria is evaluated by measurement of the inhibition zone. The results are reported in Table III.

TABLE II

| Reactant | Amount of Product (mg.) | Description of Product |
| --- | --- | --- |
| methanol | 7 | lemon yellow |
| ethanol, 95% | 6 | lemon yellow |
| n-propanol | 20 | lemon yellow |
| isopropanol, anhydrous 99% | 50 | lemon yellow |
| n-butanol | 18 | lemon yellow |
| 1-decanol | 0 | hazy |
| 2-ethyl hexanol | 0 | hazy |
| allyl alcohol | 5 | lemon yellow |
| amyl alcohol | 4 | lemon yellow |
| t-amyl alcohol | 7 | lemon yellow |
| octyl alcohol | 2 | lemon yellow |
| benzyl alcohol | 4 | lemon yellow |
| propylene glycol, U.S.P. | 72 | clear lemon yellow |
| glycerin (synthetic 99.5%) | 59 | clear lemon yellow |
| glycerin (U.S.P. 99.5%) | 64 | clear lemon yellow |
| glycerin (U.S.P. 96%) | 65 | clear lemon yellow |
| triethylene glycol | 46 | clear lemon yellow |
| tetraethylene glycol | 61 | clear lemon yellow |
| dipropylene glycol | 63 | clear lemon yellow |
| tripropylene glycol | 51 | clear lemon yellow |
| ethylene glycol n-butyl ether | 48 | clear lemon yellow |
| ethylene glycol ethyl ether | 49 | clear lemon yellow |
| diethylene glycol n-butyl ether | 52 | clear lemon yellow |
| diethylene glycol methyl ether | 47 | clear lemon yellow |
| polyethylene glycol | 31 | clear lemon color |
| acetone | 21 | light yellow |
| methyl ethyl ketone | 2 | lemon yellow |
| benzene | 3 | light yellow |
| xylene | 1 | hazy yellow |
| ether | 0 | light clear yellow |
| cyclohexane | 1 | hazy yellow |
| chloroform | 0 | light clear yellow |
| methyl chloroform | 0 | light clear yellow |
| methylene chloride | 0 | light yellow |
| tetrachloroethylene | 0 | light yellow |

TABLE III

| Composition | Dilution | Zone of Inhibition |
| --- | --- | --- |
| Crystals from propylene glycol | 1 to 100 | 10 mm |
| Liquid reaction product from propylene glycol | 1 to 100 | 2 mm |
| Liquid reaction product from propylene glycol | full strength | 4.5 mm |
| Crystals from acetone | 1 to 100 | 5 mm |
| Liquid reaction product from acetone | 1 to 100 | no overgrowth |

TABLE III-continued

| Composition | Dilution | Zone of Inhibition |
| --- | --- | --- |
| Liquid reaction product from acetone | full strength | 1 mm |
| Crystals from isopropanol | 1 to 100 | 5.5 mm |
| Liquid reaction product from isopropanol | 1 to 100 | no overgrowth |
| Liquid reaction product from ispropanol | 1 to 100 | 1.5 mm |
| Propylene glycol (control) | 1 to 100 | no overgrowth |
| Propylene glycol | full strength | 2.5 mm |

EXAMPLE 6

Ten (10) white albino rabbits, 120 days old and having body weights or 1310 to 1350 gums. are examined for normalcy and skin condition. The animals are then isolated in separate holding cages and allowed food and water ad libitum. After 7 days of observation, the bellies of the rabbits are clipped free from hair and their skin is examined to determine that it is normal. The reaction product produced in Example 1 (CA-90 Base) is applied to five animals in a 5% solution in Tween-80 and to five other animals in a 2% solution in a commercial cleansing cream. The skin area is thoroughly dried with a hair dryer before application. After dosing, the animals are wrapped in a plastic film to prevent evaporation. After 24 hrs. exposure, the covering bandage and plastic wrap are removed and the exposed skin areas examined, washed with lukewarm water and soap, rinsed and dried, and then reexamined for irritation, edema or erythema. The animals' skins are found to be uniformly soft and smooth with no irritation or sensitization. It is concluded that cosmetic creams containing the first reaction products of this invention would be of great value as skin conditioners.

The reaction product of Examples 3 and 4 is incorporated into corn oil and commercially available cosmetic bases, and is applied in both of these forms and in undiluted form to the hands of human volunteers. It is found to leave the hands in uniformly smooth and soft condition, again indicating the utility of the intermediate composition of this invention as a cosmetic skin conditioning agent.

EXAMPLE 7

A suntanning lotion is prepared having the following formulation in parts by weight:

| | |
| --- | --- |
| Component A | |
| Cetyl alcohol | 0.5 |
| Stearic acid (Emergy No. 132 lb) | 3.5 |
| Glycerol ricinoleate | 2.5 |
| 2-amino-2-methyl-1,3-propanediol | 0.25 |
| Silicone L-45 (viscosity-350 cstks.) | 3.75 |
| Isopropyl myristate | 1.0 |
| Isobutyl-p-aminobenzoate | 2.0 |
| Allantoin | 0.5 |
| Benzocain NF | 0.25 |
| Component B | |
| Veegum (R.T. Vanderbilt) | 0.5 |
| Propylene glycol U.S.P. | 6.0 |
| Methyl paraben U.S.P. | 0.125 |
| Triethanolamine | 0.25 |
| Titanium dioxide | 0.5 |
| Water (soft) | 77.4375 |
| Component C | |
| CA-90 Base (Example 4) | 0.5 |
| Calomin | 0.5 |
| Detamide (diethyltolvamide) | 0.25 |

The ingredients of Components A and B are separately mixed, melted, and heated to a temperature of 170° F. The components are then mixed by adding A to B using a high speed mixer. The mixing is continued with cooling to 130° F, and Component C is then added. Mixing and cooling continue to room temperature, and the product is then allowed to stand overnight, remixed and bottled.

EXAMPLE 8

A cream hair rinse composition is prepared having the following formulation, in parts by weight:

| | |
| --- | --- |
| Component A | |
| Triton X-400 | 8.0 |
| Cerasynt 660 (Dow Corning) | 2.5 |
| Sodium chloride | 0.5 |
| CA-90 Base (Example 4) | 1.5 |
| Water (deionized) | 87.5 |
| Component B | |
| Citric acid q.s. to pH 3.0–3.5 | |
| Component C | |
| Perfume 0136 Van Dyk | 0.3 |
| Color | qs |

The ingredients of Component A are heated at 70° to 75° C until homogeneous, and then removed from the heat and cooled to 40°–45° C. Component B is added with agitation. Component C is then added and the agitation is continued until all ingredients are thoroughly dispersed. The product is then filled into containers.

EXAMPLE 9

A night cream product is prepared in this example, having the following formulation, in parts by weight:

| | |
| --- | --- |
| Component A | |
| Lanolin (anhydrous) U.S.P. | 3.0 |
| Cetyl alcohol | 1.0 |
| Stearic acid (triple-pressed) | 10.0 |
| Isopropyl myristate | 5.0 |
| Mineral oil (light) U.S.P. | 22.0 |
| Igepal CO 630 (General Aniline) | 1.5 |
| Propyl paraben U.S.P. | 0.125 |
| Allantoin | 0.5 |
| Component B | |
| Methyl paraben U.S.P. | 0.0675 |
| Water | 47.2975 |
| Veegum (R.T. Vanderbilt) | 0.75 |
| Component C | |
| Carboxymethyl cellulose (7-HP) | 0.25 |
| Component D | |
| Sorbitol solution U.S.P. | 5.0 |
| Triethanolamine | 2.75 |
| Component E | |
| CA-90 Base (Example 4) | 0.5 |

The ingredients of Component A are melted and heated to 160° F. Component B is prepared by heating the water to 170° F and adding the methylparaben, using a high speed mixer, followed by Veegum. As soon as Component B is homogeneous, Component C is added to it and mixed until smooth. Component A is added to Components B–C with mixing, and Component D is then added. The resulting mixture is cooled to 120° F and the CA-90 Base (Component E) is added with mixing. The product is cooled to room temperature, allowed to sit for 24 hours and filled into containers. Tests show it to be an excellent skin conditioner.

EXAMPLE 10

A moisture foundation cream is prepared having the following formulation, in part by weight:

| | |
|---|---|
| Component A | |
| Lanolin (anhydrous) U.S.P. | 0.75 |
| Isopropyl myristate | 2.00 |
| Stearic acid (triple-pressed) | 14.00 |
| Cetyl alcohol | 1.00 |
| Propyl paraben U.S.P. | 0.0625 |
| Component B | |
| Methyl paraben U.S.P. | 0.125 |
| Water (soft) | 59.3125 |
| Veegum (R.T. Vanderbilt) | 0.5 |
| Allantoin | 0.5 |
| Component C | |
| Potassium hydroxide (36° Be) | 0.5 |
| Triethanolamine | 0.375 |
| Sorbitol solution U.S.P. | 4.0 |
| Glycerin U.S.P. | 16.00 |
| Component D | |
| CA-90 Base (Example 4) | 0.5 |
| Perfume | 0.375 |

Component A is melted and brought to a temperature of 170° F. The ingredients of Component B are mixed with a high speed mixer until dissolved and heated to 170° F. The ingredients of Component C are heated to 170° F and mixed with Component B. Component A is mixed with Components B and C with a high speed mixer and the resulting mixture is cooled to 130° F and Component D is added. The product is cooled to room temperature, allowed to stand overnight, remixed and filled.

Use of this formulation is shown to produce inproved skin conditioning.

EXAMPLE 11

A skin freshener composition is prepared by mixing the following ingredients, in parts by weight:

| | |
|---|---|
| Ethyl alcohol (39C) | 17.10 |
| Carbitol | 6.40 |
| CA-90 Base (Example 4) | 2.00 |
| Benzoic acid | 0.19 |
| Perfume (Orange Fluerr M-11'9) | 0.13 |
| Distilled water | 102.08 |

EXAMPLE 12

A hand and body lotion composition is prepared having the following formulation, in parts by weight:

| | |
|---|---|
| Component A | |
| Mineral oil (light) | 2.50 |
| Standamul 1414-E (Atlas Chemical) | 2.50 |
| Stearic Acid (triple-pressed) | 2.60 |
| Tegin (Churchill Co.) | 1.50 |
| Acetulan (Churchill Co.) | 1.00 |
| Allantoin | 0.20 |
| Lantrol (Dow Chemical) | 0.50 |
| Propyl p-hydroxybenzoate | 0.10 |
| Component B | |
| CA-90 Base (Example 4) | 1.00 |
| Triethanolamine (95–99%) | 0.70 |
| Methyl p-hydroxybenzoate | 0.10 |
| Propylene glycol U.S.P. | 1.00 |
| Water | 86.25 |

Components A and B are separately heated to 175° F and Component B is then slowly added to Component A with constant agitation. Perfume and color are added as desired at 100° F and the product is then cooled and filled.

EXAMPLE 13

A cleansing cream composition is prepared having the following formulation in parts by weight:

| | |
|---|---|
| Component A | |
| Lanolin (anhydrous) U.S.P. | 3.0 |
| Cetyl alcohol | 1.0 |
| Oleic acid | 7.0 |
| Isopropyl myristate | 5.0 |
| Mineral oil (Light) U.S.P. | 33.5 |
| Igepal CO 630 | 2.0 |
| Propyl paraben | 0.125 |
| Allantoin | 0.5 |
| Component B | |
| Methyl paraben | 0.0675 |
| Water | 41.5 |
| Veegum (R.T. Vanderbilt) | 0.25 |
| Component C | |
| Carboxymethyl cellulose (7-HP) | 0.25 |
| Component D | |
| Glycerin U.S.P. | 3.0 |
| Triethanolamine | 2.0 |
| Component E | |
| CA-90 Base (Example 4) | 0.5 |

The ingredients of Component A are melted and brought to a temperature of 170° F. The water of Component B is heated to 160° F and the methyl paraben and then the Veegum are added. Component D is added to the B-C mixture, followed by addition of Component A. Mixing is continued with cooling to 120° F and Component E is then added. The product is allowed to stand 24 hours and filled. This formulation is tested and found to produce improved skin conditioning.

EXAMPLE 14

A protein anti-dandruff shampoo composition is prepared by admixing the following ingredients in the amounts shown in parts by weight:

| | |
|---|---|
| Potassium salt of undecylenyl-polypeptide condensate | 20.00 |
| Potassium salt of cocoyl-polypeptide condensate | 25.00 |
| Sodium salt of collagen protein hydrolysate | 5.00 |
| Sodium lauryl ether sulfate | 47.5 |
| CA-90 Base (Example 4) | 2.00 |
| Herbal extracts as a perfume | 0.5 |

EXAMPLE 15

A suntan lotion composition is prepared having the following formulation, in parts by weight:

| | |
|---|---|
| Glyceryl para-aminobenzoate | 1.5 |
| Mineral oil (light) | 4.0 |
| Isopropyl myristate | 4.0 |
| Isopropyl alcohol (anhyd) | 28.5 |
| Dipropylene glycol | 28.0 |
| CA-90 Base (Example 4) | 1.5 |
| Gentron-11 (Freon) | 32.5 |
| Perfume | gs. |

The aminobenzoate is dissolved in isopropyl alcohol, and mineral oil isopropyl myristate, glycol and CA-90 Base are added to the mixture. The Freon is then added with stirring. This mixture exists as two phase liquid until the gas (Freon 12) is subsequently added. A side seam, unlined standard container having a standard valve with mechanical breakup and actuator is filled with a mixture of 75 parts by weight of this product and 25% parts by weight of Freon-12 gas to produce the final suntan lotion product.

The present invention in its broader aspects is not limited to the specific details shown and described above, but departures may be made from such details without departing from the principles of the invention and without sacrificing its chief advantages.

What is claimed is:

1. A process for preparing an organic composition which comprises contacting the pulps of grapefruit with a non-toxic polyhydric alcohol to form a reaction product and separating this product from the pulp residue.

2. The process of claim 1 wherein the polyhydric alcohol is selected from the group consisting of propylene glycol and glycerin.

3. The process of claim 2 wherein the grapefruit pulp is the inner pulp of fresh grapefruit having a pH of about 2.5 to 5.0.

4. The process of claim 2 wherein the grapefruit pulp is contacted with the polyhydric alcohol at a weight ratio of about 1:2, and the reaction is carried out at an elevated temperature.

5. The process of claim 1 wherein the grapefruit pulp is contacted with propylene glycol.

6. The process of claim 1 wherein the grapefruit pulp is contacted with glycerin.

7. A process for forming an organic composition which comprises contacting fresh grapefruit pulp having a low acid content, as shown by a pH of about 2.5 to 5.0, with an excess of propylene glycol or glycerin at a temperature of about 90° to 140° F. for a period of about 6 to 24 hours to form a reaction product and separating the product from the pulp residue.

8. An organic composition comprising the product obtained by contacting grapefruit pulp with a non-toxic polyhydric alcohol to form a reaction product, and separating this product from the pulp residue.

9. The composition of claim 8 wherein the polyhydric alcohol is propylene glycol or glycerin.

10. The composition of claim 8 wherein the grapefruit pulp is fresh grapefruit pulp having a pH of about 2.5 to 5.0.

11. The composition of claim 10 wherein the polyhydric alcohol is propylene glycol.

12. The composition of claim 11 where an excess of propylene glycol is contacted with the grapefruit pulp at a temperature of about 90° to 140° F. for a period of about 6 to 24 hours.

13. The composition of claim 8 wherein the polyhydric alcohol is contacted with the grapefruit pulp in the presence of a free radical initiator.

* * * * *